United States Patent [19]

Okorodudu

[11] 4,250,314

[45] Feb. 10, 1981

[54] ADDUCTS OF PHOSPHOROUS TRIAMIDES AND α, β UNSATURATED CARBONYL COMPOUNDS

[75] Inventor: Abraham O. Okorodudu, West Deptford, N.J.

[73] Assignee: Mobil Oil Corporation, New York, N.Y.

[21] Appl. No.: 34,814

[22] Filed: Apr. 30, 1979

Related U.S. Application Data

[62] Division of Ser. No. 866,579, Jan. 3, 1978, Pat. No. 4,183,817.

[51] Int. Cl.$^3$ .................... C07F 9/28; C07C 101/02; C07C 101/20; C07C 101/44

[52] U.S. Cl. ........................................ 546/21; 546/22; 560/155; 560/171; 560/43; 560/44; 560/38; 560/121; 560/125; 260/326.61; 260/326.43; 260/326.25

[58] Field of Search ................. 560/155, 171, 43, 44, 560/38, 121, 125; 260/326.61, 326.43, 326.25; 546/21, 22

[56] References Cited

U.S. PATENT DOCUMENTS 3,496,231  2/1970  Maier ............................. 260/326.61

*Primary Examiner*—Henry R. Jiles
*Assistant Examiner*—Robert C. Whittenbaugh

[57] ABSTRACT

Adducts of alkylphosphorous triamides with alpha, beta-unsaturated carbonyl compounds provide novel sulfur-free load-carrying additives for various organic compositions, e.g., lubricant oils.

16 Claims, No Drawings

ADDUCTS OF PHOSPHOROUS TRIAMIDES AND α, β UNSATURATED CARBONYL COMPOUNDS

This is a division of copending application Ser. No. 866,579, filed Jan. 3, 1978 and now U.S. Pat. No. 4,183,817.

BACKGROUND OF THE INVENTION

1. Field of the Invention

This application is directed to oil-soluble, sulfur-free load-carrying additives comprising novel adducts of phosphorous triamides and alpha, beta unsaturated carbonyl compounds. This application is also directed to organic compositions, e.g., lubricant compositions containing said novel adducts.

2. Description of the Prior Art

The use of phosphorus compounds as load-carrying or antiwear agents in lubricant compositions is known. Also, the use of phosphorus compounds in combination with organic materials is known. For example, U.S. Pat. Nos. 3,115,465 and 3,986,967 disclose the use of phosphorus compounds in combination with hindered phenols or benzotriazole as lube oil additives.

SUMMARY OF THE INVENTION

This application, however, is directed to the discovery of adducts of phosphorus, e.g., hexaalkyl phosphorous triamides and alpha, beta-unsaturated carbonyls, e.g., methyl acrylate as novel compounds and load-carrying additives for various organic media, e.g., oils of lubricating viscosity or greases prepared therefrom.

The application is therefore also directed to lubricant compositions having a major proportion of, for example, a lubricant and a minor load-carrying proportion of the hereindescribed novel adducts.

The novel compounds have the following general structure

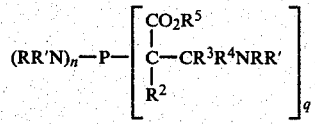

where n is 0, 1 or 2; q is 1, 2 or 3, with the proviso that the sum of n and q equals 3 and where R and R' are each selected from alkyl of from 1 to about 32 carbon atoms, aryl, aralkyl or alkaryl of 6 to about 30 carbon atoms. R and R' may be alicyclic ($C_mH_{2m-1}$) such as cyclopentyl ($C_5H_9-$) or cyclohexyl ($C_6H_{11}-$) and RR' may be $(CH_2)_m$ comprising part of a heterocyclic system such as ($-CH_2-$)$_4$ in pyrrolidine or ($-CH_2-$)$_5$ in piperidine. $R^2$, $R^3$ and $R^4$ may be H, or alkyl of 1 to 32 carbon atoms or aryl, aralkyl, alkaryl of 6 to 30 carbon atoms, and $R^5$ may be alkyl, or hereto substituted alkyl of 1 to 30 carbon atoms, aryl, aralkyl or alkaryl of 6 to 30 carbon atoms.

The preferred novel compounds in accordance with this invention have the following general structure

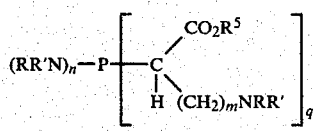

where the substituents are as defined above. The phosphorous triamides useful in this invention have the following general formula:

$$(RR'N)_3P$$

where R and R' are as previously described. They may be obtained commercially or synthesized in any convenient manner known to the art. For example, any secondary amine such as dimethylamine may be reacted in the following manner with a phosphorus halide $PX_3$ (X may be bromo, chloro or iodo) such as $PCl_3$ under appropriate reaction conditions to yield the desired triamide:

$$6RR'NH + PCl_3 \rightarrow (RR'N)_3P + 3RR'NH_2Cl.$$

Any suitable secondary amine, RR'NH, may be used, e.g., diethylamine, N-methylaniline and so on. R and R' are as previously described. The phosphorous triamide is then reacted with a carbonyl-containing compound according to the general procedure below which exemplifies methyl acrylate:

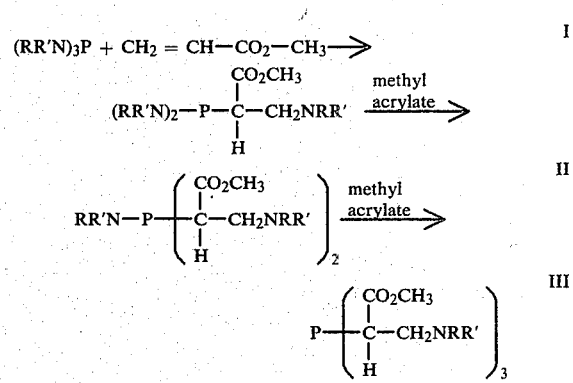

The reaction is exothermic with temperatures occasionally exceeding 110° C. General reaction conditions include room temperature to 200° C. and preferably room to 85° C., atmospheric pressure or higher if desired with reaction times ranging from 1 to 6 hours.

The R group in the organophosphorus reactants are hydrocarbyl containing up to 32 carbon atoms, which can be alkyl, aromatic or alkyl-substituted aromatic. The aromatic groups include phenyl, naphthyl and anthryl, and those members substituted with a $C_1-C_{18}$ alkyl. Such alkyl groups include methyl, butyl, octyl, decyl, dodecyl, tetradecyl, octadecyl and the like, and it will be understood that the mention of each of these is a disclosure of its attachment to each of the aromatic groups mentioned and the incorporation of the alkylaromatic compound into the various final products contemplated by this invention. Finally, the alkyl group R can also have from 1 to 32 carbon atoms and includes methyl, ethyl, hexyl, nonyl, tetradecyl and octadecyl, eicosyl, pentacosyl, triacontyl and dotriacontyl. Here again, the disclosure of each of these groups is a disclosure of their incorporation in all the various final products of this invention.

Suitable carbonyl compounds include any suitable alpha, beta, unsaturated carbonyls such as methyl acrylate, 2-ethylhexyl acrylate, dimethylaminoethyl methacrylate, stearyl methacrylate, ethyl cinnamate, ethyl crotonate, ethyl maleate, methyl vinyl ketone, etc.

The compounds of this invention are especially effective in lubricant compositions in which the lubricant base is a petroleum product, such as a mineral lubricating oil, a synthetic lubricant fluid or an ester-base oil. Such synthetic fluids include synthetic hydrocarbon oils derived from long chain alkanes or olefin polymers, ester oils obtained from polyhydric alcohols and monocarboxylic acids or monohydric alcohols and polycarboxylic acids. Also the lubricant herein includes greases made from the named classes of lubricant compositions and/or fluids.

The concentration of additive may vary from about 0.05 to about 10% by weight. Optimum performance characteristics are evidenced by lubricants containing from about 0.25% to about 2% by weight of the additives of this invention, and this is the preferred range of concentration.

The following examples are offered as illustrations of the invention.

EXAMPLE 1

Preparation of Tri[1-carbomethoxy-2-tetramethylene-amino ethyl]phosphine

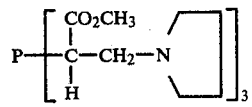

To a stirred solution of methyl acrylate (129 g., 1.5 moles) and 100 ml of 2-methoxyethyl ether (diglyme) at room temperature in a 500 ml reaction flask protected from moisture, was added dropwise, 53.2 g. (0.2 moles) of tris[tetramethylene]phosphorous triamide. After the addition and the ensuing exothermic reaction had subsided (temperature rose to 120° C.) the reaction mixture was refluxed for 3½ hours and then stripped under vacuum.

EXAMPLE 2

Preparation of Tri[1-carbomethoxy-2-pentamethylene-amino ethyl]phosphine

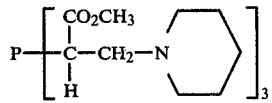

This compound was prepared as outlined in Example 1 except that tris pentamethylenephosphorous triamide was used.

EXAMPLE 3

Preparation of Tri[1-carbomethoxy-2-N,N,diethylamino ethyl]phosphine

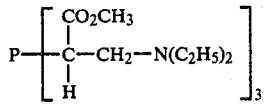

This was prepared as outlined in Example 1 except that hexaethylphosphorous triamide was used.

EXAMPLE 4

Preparation of Tri[1-carbomethyoxy-2-N,N,dibutylamino-ethyl]phosphine

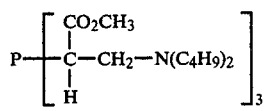

This compound was prepared as outlined in Example 1 except that hexabutylphosphorous triamide was used.

The additives prepared in the above examples were evaluated in the standard 4-Ball Wear Test using ½ inch 52100-steel balls at a load of 60 kilograms for 30 minutes under the conditions set forth in the table below. The oil used was an 80/20 mixture of a solvent refined Mid-Continent paraffinic 150/160 second bright mineral oil.

The data in the table clearly establish that the lubricant additives in accordance herewith possess good load-carrying properties.

It is understood that only preferred embodiments have been exemplified, which in no way limit the specification or claims, departure therefrom is within the skill of the art.

TABLE

| | | | | 4-Ball Wear Scar Diam (mm) ½" Balls, 52100 Steel, 60 kg, 30 minutes | | | | |
|---|---|---|---|---|---|---|---|---|
| | | Conc. | Temp. | SPEED (RPM) | | | | |
| Ex. | Additive | Wt. % | °F. | 500 | 1000 | 1500 | 2000 | |
| | None (base stock mineral oil) | 100 | Room | 0.50 | 0.60 | 0.88 | 2.34 | |
| | | | 200 | 0.60 | 1.06 | 1.86 | 2.23 | |
| | | | 390 | 1.0 | 1.31 | 2.06 | | |
| 1 | 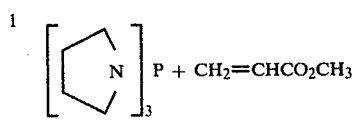 | 1 | Room | 0.40 | 0.50 | 0.50 | 0.50 | |
| | | | 200 | 0.50 | 0.50 | 0.50 | 0.50 | |
| | | | 390 | 0.60 | 0.50 | 0.70 | 0.70 | |

TABLE-continued

| | | | | 4-Ball Wear Scar Diam (mm) $\frac{1}{2}''$ Balls, 52100 Steel, 60 kg, 30 minutes | | | | |
|---|---|---|---|---|---|---|---|---|
| Ex. | Additive | Conc. Wt. % | Temp. °F. | SPEED (RPM) | | | | |
| | | | | 500 | 1000 | 1500 | 2000 | |
| 2 | 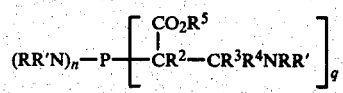 | 1 | Room | 0.40 | 0.40 | 0.50 | 0.50 | |
| | | | 200 | 0.50 | 0.50 | 0.50 | 0.70 | |
| | | | 390 | 0.80 | 1.0 | 0.70 | 0.80 | |
| 3 | $[(C_2H_5)_2N]_3P + CH_2=CHCO_2CH_3$ | 1 | Room | 0.40 | 0.50 | 0.60 | 0.70 | |
| | | | 200 | 0.50 | 0.50 | 0.60 | 0.65 | |
| | | | 390 | 0.60 | 0.70 | 1.05 | 1.50 | |
| 4 | $[(C_4H_9)_2N]_3P + CH_2=CHCO_2CH_3$ | 1 | Room | 0.40 | 0.40 | 0.50 | 0.60 | |
| | | | 200 | 0.40 | 0.50 | 0.50 | 0.50 | |
| | | | 390 | 0.50 | 0.60 | 1.0 | — | |

What is claimed is:

1. A compound of the formula $$(RR'N)_n-P \left[ \begin{array}{c} CO_2R^5 \\ | \\ CR^2-CR^3R^4NRR' \end{array} \right]_q$$

where n is 0,1 or 2; q is 1, 2 or 3 with the proviso the sum of n and q equals 3 and where R and R' are each selected from alkyl of 1 to about 32 carbon atoms, aryl, aralkyl or alkaryl of 6 to about 30 carbon atoms and alicyclic ($C_mH_{2m-1}$) and RR' may be $(CH_2)_m$ comprising part of a heterocyclic system selected from, pyrolidine or piperidine and where m is from 2 to 6; $R^2$, $R^3$ and $R^4$ may be H, or alkyl of 1 to 32 carbon atoms or aryl, alkaryl or aralkyl of 6 to 30 carbon atoms and $R^5$ may be alkyl or nitrogen-substituted alkyl of 1 to 30 carbon atoms, aryl, alkaryl or aralkyl of 6 to 30 carbon atoms.

2. The compound of claim 1 having the formula

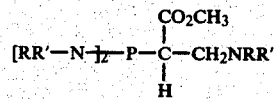

3. The compound of claim 1 having the formula

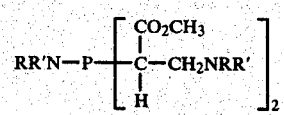

4. The compound of claim 1 having the formula

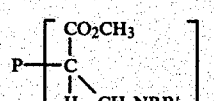

5. The compound of claim 4 where R and R' are each alkyl of 1 to about 12 carbon atoms.

6. The compound of claim 5 where R is ethyl, R' is ethyl and q is 3.

7. The compound of claim 5 where R is butyl, R' is butyl and q is 3.

8. The compound of claim 1 where RR'N is a heterocyclic moiety selected from

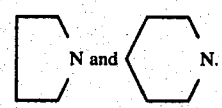

9. The compound of claim 8 where RR'N is

10. The compound of claim 8 where RR'N is

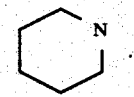

11. The compound of claim 1 having the formula

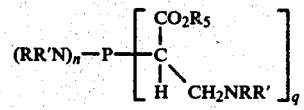

12. The compound of claim 2 having the formula

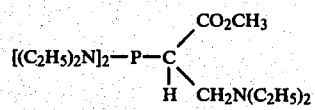

13. The compound of claim 2 having the formula

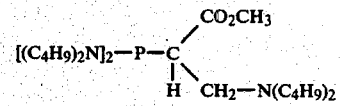

14. The compound of claim 1 having the formula

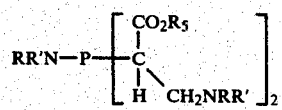

15. The compound of claim 3 having the formula
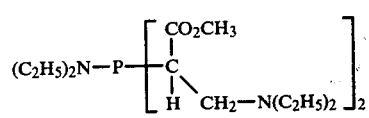
16. The compound of claim 1 having the formula
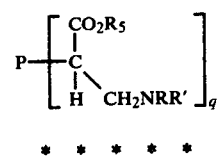
* * * * *

UNITED STATES PATENT AND TRADEMARK OFFICE
CERTIFICATE OF CORRECTION

PATENT NO. : 4,250,314

DATED : February 10, 1981

INVENTOR(S) : Abraham O. Okorodudu

It is certified that error appears in the above—identified patent and that said Letters Patent are hereby corrected as shown below:

Col. 1, line 69: "$(CH_2)_m$" should be --$(CH_2)$--.

Signed and Sealed this

Twenty-first Day of July 1981

[SEAL]

Attest:

Attesting Officer

GERALD J. MOSSINGHOFF

Commissioner of Patents and Trademarks